US00PP12656P2

(12) United States Plant Patent
Walker

(10) Patent No.: US PP12,656 P2
(45) Date of Patent: May 28, 2002

(54) BEGONIA PLANT NAMED 'DOUBLET PINK'

(75) Inventor: Trevor C. Walker, La Roche Bernard (FR)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/606,140

(22) Filed: Jun. 28, 2000

(51) Int. Cl.[7] ..... A01H 5/00
(52) U.S. Cl. ..... Plt./343
(58) Field of Search ..... Plt./343, 348

(56) References Cited

U.S. PATENT DOCUMENTS

PP10,736 P * 12/1998 McCullough ..... Plt./343

* cited by examiner

*Primary Examiner*—Bruce R. Campell

*Assistant Examiner*—Susan B. McCormick

(74) *Attorney, Agent, or Firm*—C. A. Whealy

(57) ABSTRACT

A new and distinct cultivar of Begonia plant name 'Doublet Pink'. characterized by its somewhat upright, rounded, uniform, and compact plant habit; small dark greenish bronze leaves; freely branching, dense and bushy growth habit; continuous and very freely flowering habit; showy, fully double pink-colored flowers that are displayed above and beyond the foliage; and tolerance to pathogens common to Begonias.

1 Drawing Sheet

BACKGROUND OF THE INVENTION

The present Invention relates to a new and distinct cultivar of Begonia, botanically known as *Begonia semperflorens*, and hereinafter referred to by the cultivar name 'Doublet Pink'.

The new Begonia is a product of a planned breeding program conducted by the Inventor in Poland. The objective of the breeding program is to create new Begonia varieties having compact plant habit and numerous fully-double flowers.

The new Begonia originated from a cross made by the Inventor in 1990 in Poland of a proprietary Begonia seedling selection identified as BD1 as the female, or seed, parent with a proprietary Begonia seedling selection identified as MD7 as the male, or pollen, parent. The new Begonia was discovered and selected by the Inventor as a flowering plant within the progeny of the stated cross in a controlled environment in Poland in 1996. The selection of this plant was based on its compact plant habit and numerous double flowers. These characteristics differentiate the new Begonia from its parent selections.

Asexual reproduction of the new Begonia by terminal cuttings taken in a controlled environment in Poland, has shown that the unique features of this new Begonia are stable and reproduced true to type in successive generations.

SUMMARY OF THE INVENTION

The new Begonia has not been observed under all possible environmental conditions. The phenotype may vary somewhat with variations in environments such as temperature, daylength, light intensity, nutritional and water status without, however, any variance in genotype. The following traits have been repeatedly observed and are determined to be the unique characteristics of 'Doublet Pink'. These characteristics in combination distinguish 'Doublet Pink' as a new and distinct cultivar:

1. Somewhat upright, rounded, uniform, and compact plant habit.
2. Small dark greenish bronze leaves.
3. Freely branching, dense and bushy growth habit.
4. Continuous and very freely flowering habit.
5. Showy, fully double pink-colored flowers that are displayed above and beyond the foliage.
6. Tolerant to pathogens common to Begonias.

BRIEF DESCRIPTION OF THE PHOTOGRAPH

The accompanying colored photograph illustrates the overall appearance of the new Begonia. This photograph shows the colors as true as it is reasonably possible to obtain in colored reproductions of this type. Colors in the photograph may differ slightly from the color values cited in the detailed botanical description, which more accurately describe the actual colors of the new Begonia. The photograph comprises a side perspective view of a typical plant of 'Doublet Pink'.

DETAILED BOTANICAL DESCRIPTION

The aforementioned and following observations, measurements and values describe plants grown in a fiberglass-covered greenhouse in Lompoc, Calif., during the spring under conditions which approximate commercial production practices. After the cuttings were rooted, plants were planted in 10-cm containers and grown for about 10 weeks with day temperatures ranging from 21 to 24° C., night temperatures ranging from 16 to 18° C., and light levels ranging from 3,000 to 4,000 foot-candles. In the following description, color references are made to The Royal Horticultural Society Colour Chart except where general terms of ordinary dictionary significance are used.

Botanical classification: *Begonia semperflorens* cultivar Doublet Pink.

Parentage:

*Female or seed parent*.—Proprietary *Begonia semperflorens* seedling selection identified as BD1, not patented.

*Male or pollen parent*.—Proprietary *Begonia semperflorens* seedling selection identified as MD7, not patented.

Propagation:

*Type*.—By terminal vegetative cuttings.

*Time to initiate roots*.—Summer: About 10 days at 21° C. Winter: About 12 days at 21° C.

*Time to develop roots*.—Summer: About 28 days at 21° C. Winter: About 28 days at 21° C.

*Rooting habit*.—Numerous, fine, fibrous, well-branched.

Plant description:

*Plant form and growth habit*.—Compact; somewhat upright, rounded, uniform plant habit; dense and bushy growth habit. Flowers are fully double and abundant; flowering continuous. Moderately vigorous.

*Crop time*.—To produce a 10-cm container flowering plant, about 6 to 8 weeks are required after planting a rooted cutting. To produce a 15-cm or larger container flowering plant, about 8 to 10 weeks are required after planting a rooted cutting.

*Appropriate containers*.—One plant is typically planted in 10 to 15-cm containers. Multiple plants are typically planted in containers larger than 15-cm.

*Branching habit*.—Very freely and self-branching with about ten lateral branches per plant.

*Plant height, soil level to top of flowers*.—About 17.5 cm.

*Lateral branch description*.—Length: About 14 cm. Diameter at base: About 7 mm. Internode length: About 2 cm.

Foliage description:

*Arrangement*.—Alternate, single; densely foliated, about 5 to 10 or more leaves per lateral branch.

*Length*.—About 5.5 cm.

*Width*.—About 6 cm.

*Shape*. —Reniform.

*Apex*.—Acute.

*Base*.—Cordate, not equilateral.

*Margin*.—Slightly serrate with fine ciliation.

*Texture*.—Smooth, glabrous, waxy and shiny.

*Venation pattern*.—Palmate.

*Color*.—Young foliage, upper surface: 147A to 147B with dark purple, 183B, cast. Young foliage, lower surface: 147A to 147B with dark purple, 183B, cast. Mature foliage, upper surface: 147A with dark purple, 183D, cast; venation, 146A. Mature foliage, lower surface: 147A with dark purple, 183D, cast; venation, 146B.

*Petiole*.—Length: About 2.5 mm. Diameter: About 4 mm. Color: 146D; petioles of young leaves with slight red purple, 185C, cast.

Flower description:

*Flowering habit*.—Fully double flowers with numerous tepals, flowers arranged in axillary cymes. Flowers above and beyond the foliage. Extremely freely flowering with usually about 25 flowers and flower buds per lateral branch and typically more than 100 flowers per plant. Many cymes in flower simultaneously. Flowering continuous. Flowers self-cleaning. Not fragrant.

*Natural flowering season*.—Plants will flower year round under greenhouse conditions.

*Flower longevity*.—Flowers last about 10 to 12 days on the plant depending on temperature.

*Flowers*.—Aspect: Mostly outwardly facing. Shape: Rounded; rose-like. Diameter: About 1.8 cm. Depth (height): About 1 cm.

*Flower bud* (*just before opening*).—Rate of opening: From full color to fully open, about 10 days are required depending on temperature. Length: About 6 mm. Diameter: About 1 cm. Shape: Oblong. Color: 55B.

*Tepals*.—Arrangement/quantity: Fully double flower form; numerous whorls of tepals arrange in a rosette; at least 75 tepals per flower. Length: About 7 mm. Width: About 6 mm.. Shape: Oblanceolate. Apex: Obtuse. Base: Acute. Margin: Entire. Texture: Smooth. Color: When opening, upper surface: 55B. When opening, lower surface: 55D. Fully opened, upper surface: 55C, fading to 55D. Fully opened, lower surface: 55D.

*Peduncles*.—Length: About 3.5 cm. Diameter: About 2 mm. Angle: About 45° from vertical. Strength: Moderate to strong. Color: Base, green, 146B, with slightly purple, 185D, cast.

*Pedicels*.—Length: About 9 mm. Diameter: About 1 mm. Color: 185C.

*Reproductive organs*.—Stamens: None observed. Pistils: None observed.

*Seed*.—Seed production has not been observed.

Disease resistance: Plants of the new Begonia have been noted to be tolerant to pathogens common to Begonias.

It is claimed:

1. A new and distinct Begonia plant named 'Doublet Pink', as illustrated and described.

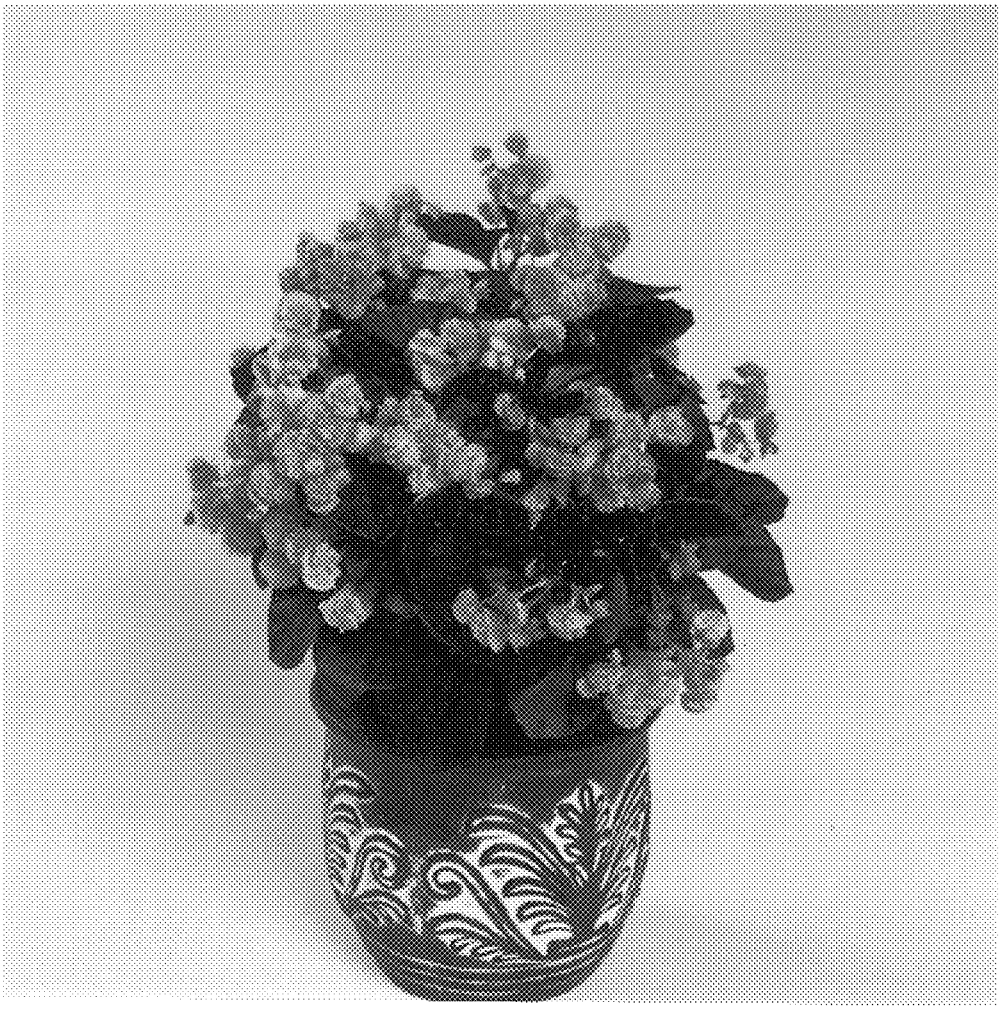

* * * * *